United States Patent
Sanchez, Jr. et al.

(10) Patent No.: US 6,617,176 B1
(45) Date of Patent: Sep. 9, 2003

(54) METHOD OF DETERMINING BARRIER LAYER EFFECTIVENESS FOR PREVENTING METALLIZATION DIFFUSION BY FORMING A TEST SPECIMEN DEVICE AND USING A METAL PENETRATION MEASUREMENT TECHNIQUE FOR FABRICATING A PRODUCTION SEMICONDUCTOR DEVICE AND A TEST SPECIMEN DEVICE THEREBY FORMED

(75) Inventors: John E. Sanchez, Jr., Palo Alto, CA (US); Pin-Chin Connie Wang, Menlo Park, CA (US); Christy Mei-Chu Woo, Cupertino, CA (US); Paul R. Besser, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/152,861

(22) Filed: May 21, 2002

(51) Int. Cl.[7] ............................................. H01L 21/66
(52) U.S. Cl. ....................... 438/14; 438/16; 438/686; 438/687; 438/720; 438/723; 438/724; 438/756; 257/412
(58) Field of Search ........................... 438/14, 16, 686, 438/687, 720, 723, 724, 756; 257/412

(56) References Cited

U.S. PATENT DOCUMENTS

| | | | | |
|---|---|---|---|---|
| 5,332,697 A | * | 7/1994 | Smith et al. ................ | 438/479 |
| 5,851,912 A | * | 12/1998 | Liaw et al. ................. | 438/621 |
| 5,923,999 A | * | 7/1999 | Balasubramanyam et al. .......................... | 438/592 |
| 6,114,736 A | * | 9/2000 | Balasubramanyam et al. .......................... | 257/412 |
| 6,294,396 B1 | * | 9/2001 | Nogami et al. .............. | 438/16 |
| 6,452,224 B1 | * | 9/2002 | Mandelman et al. ....... | 257/296 |
| 6,541,286 B1 | * | 4/2003 | Bernard et al. ............. | 438/14 |

\* cited by examiner

*Primary Examiner*—John F. Niebling
*Assistant Examiner*—Olivia Luk
(74) *Attorney, Agent, or Firm*—LaRiviere, Grubman & Payne, LLP

(57) ABSTRACT

A method (M) of determining the effectiveness of a deposited thin conformal barrier layer (30) by forming a test specimen and measuring the copper (Cu) penetration from a metallization layer (40) through the barrier layer (30) (e.g., refractory metals, their nitrides, their carbides, or their other compounds), through a thin insulating dielectric layer (20) (e.g., $SiO_2$), and into a semiconductor (10) substrate (e.g., Si), wherein the interaction between the migrating metal ions and the semiconductor ions are detected/monitored, and wherein the detection/monitoring comprises (1) stripping at least a portion of the insulating dielectric layer (20) and the barrier layer (30) and (2) examining the semiconductor substrate (10) surface of the test specimen, thereby improving interconnect reliability, enhancing electromigration resistance, improving corrosion resistance, reducing copper diffusion, and a test specimen device thereby formed.

20 Claims, 2 Drawing Sheets

Figure 1:
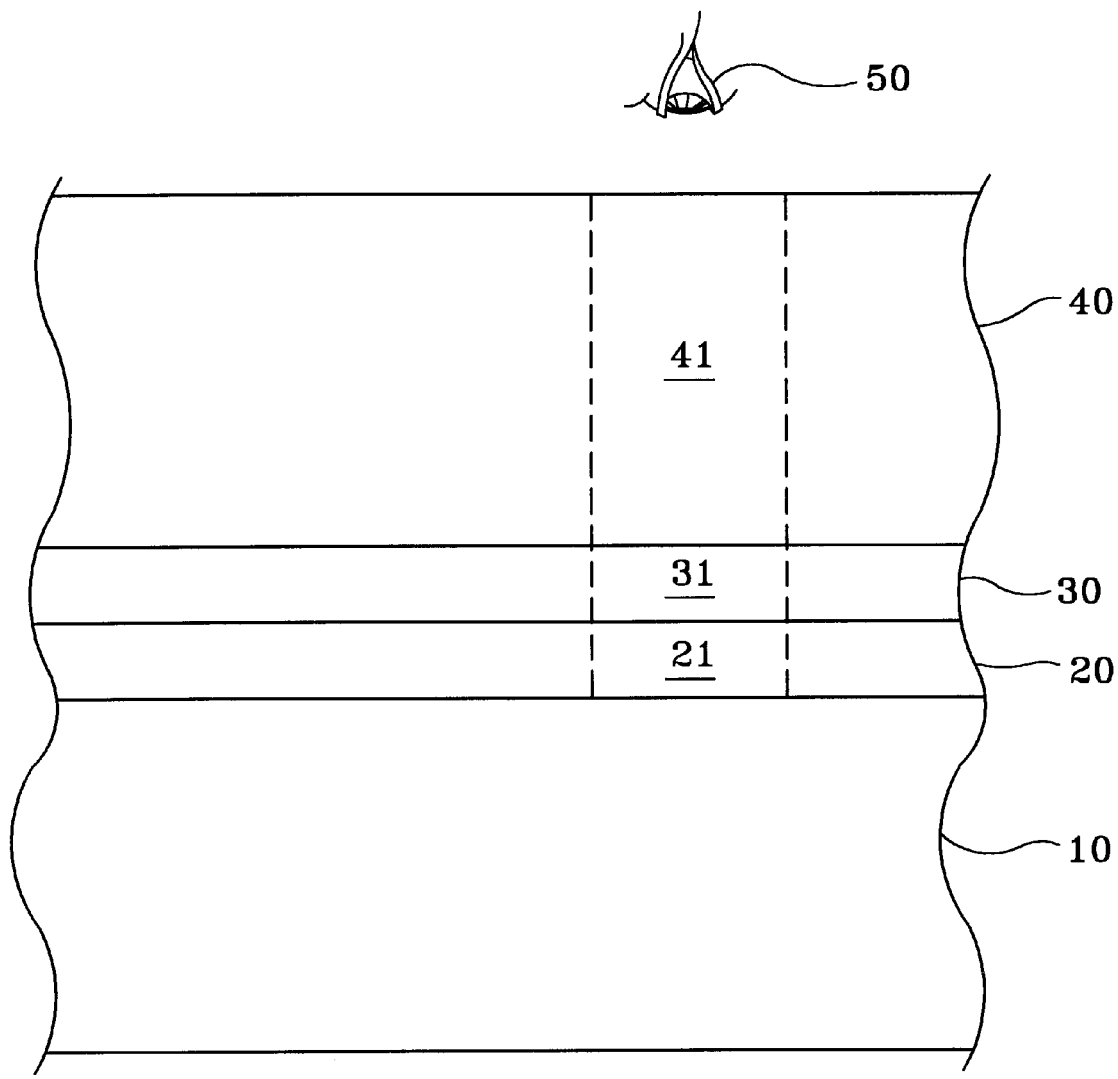

METHOD OF DETERMINING BARRIER LAYER EFFECTIVENESS FOR PREVENTING METALLIZATION DIFFUSION BY FORMING A TEST SPECIMEN DEVICE AND USING A METAL PENETRATION MEASUREMENT TECHNIQUE FOR FABRICATING A PRODUCTION SEMICONDUCTOR DEVICE AND A TEST SPECIMEN DEVICE THEREBY FORMED

TECHNICAL FIELD

The present invention relates to semiconductor devices and their methods of fabrication. More particularly, the present invention relates to the processing of copper interconnect material in conjunction with a diffusion barrier layer and the resultant device utilizing the same. Even more particularly, the present invention relates to reducing copper diffusion from copper interconnect lines into the semiconductor substrate by increasing the effectiveness of a barrier material.

BACKGROUND ART

Currently, the semiconductor industry is demanding faster and denser devices (e.g., 0.05-$\mu$m to 0.25-$\mu$m) which implies an ongoing need for low resistance metallization. Such need has sparked research into resistance reduction through the use of barrier metals, stacks, and refractory metals. Despite aluminum's (Al) adequate resistance, other Al properties render it less desirable as a candidate for these higher density devices, especially with respect to its deposition into plug regions having a high aspect ratio cross-sectional area. Thus, research into the use of copper as an interconnect material has been revisited, copper being advantageous as a superior electrical conductor, providing better wettability, providing adequate electromigration resistance, and permitting lower deposition temperatures. The copper (Cu) interconnect material may be deposited by chemical vapor deposition (CVD), plasma-enhanced chemical vapor deposition (PECVD), sputtering, electroless plating, and electrolytic plating.

However, some disadvantages of using Cu as an interconnect material include etching problems, corrosion, and diffusion into silicon. These problems have instigated further research into the formulation of barrier materials for reducing electromigration in both Al and Cu interconnect lines. In response to electromigration concerns relating to the fabrication of semiconductor devices particularly having aluminum-copper alloy interconnect lines, the industry has been investigating the use of various barrier materials such as titanium-tungsten (TiW) and titanium nitride (TiN) layers as well as refractory metals such as titanium (Ti), tungsten (W), tantalum (Ta), molybdenum (Mo), their nitrides, and their carbides.

Although the foregoing materials are adequate for Al interconnects and Al—Cu alloy interconnects, they have not been entirely effective with respect to all-Cu interconnects. In particular, the effectiveness of a deposited thin conformal diffusion barrier layer, typically comprising refractory metals and their compounds, is difficult to determine. In the related art, a "line-to-line leakage" method is used in characterizing the effectiveness of barriers in preventing Cu diffusion; however, this method introduces interfaces that created undesirable rapid Cu diffusion pathways around the barrier layer and the dielectric layer rather than through the barrier layer and the dielectric layer, thereby short-circuiting the Cu diffusion, thereby resulting in the fabrication of devices having inferior barrier layers, and thereby imparting erroneous or misleading data. Further, the line-to-line leakage method only measures electrical current. Therefore, a need exists for a low cost and high throughput method of determining the copper penetration (i.e., diffusion) from the interconnect structure (or a metallized blanket layer) through the barrier layer, through an insulating layer, and into the semiconductor substrate for fabricating a semiconductor device for improving interconnect reliability, enhancing electromigration resistance, improving corrosion resistance, and reducing copper diffusion, and a device thereby fabricated.

DISCLOSURE OF THE INVENTION

Accordingly, the present invention provides a method of determining the effectiveness of a deposited thin conformal diffusion barrier layer by forming a test specimen device and measuring the metal (e.g., Cu) penetration in the test specimen from a metallization layer through the barrier layer (e.g., refractory metals, their nitrides, their carbides, or their other compounds), through a thin insulating layer (e.g., $SiO_2$), and into a semiconductor substrate (e.g., Si), under accelerated test conditions, for fabricating a production semiconductor device, wherein the interaction between the migrating metal ions and the semiconductor ions are detected/monitored, and wherein the detection/monitoring generally comprises: (1) stripping at least a portion of the insulating layer and the barrier layer; (2) examining the semiconductor substrate surface; and (3) adjusting the parameters for forming the barrier layer, thereby improving interconnect reliability, enhancing electromigration resistance, improving corrosion resistance, and reducing copper diffusion, and a test specimen device thereby formed.

By example only, the present invention involves a method comprising: (a) providing a semiconductor substrate for forming a test specimen; (b) forming a thin insulating dielectric layer on the semiconductor substrate; (c) forming a thin diffusion barrier layer on the thin insulating dielectric layer; (d) forming a metallized blanket layer on the diffusion barrier layer; (e) treating the blanket layer with at least one technique selected from a group consisting essentially of (1) heating the blanket layer and (2) applying a voltage bias to the blanket layer for instigating the metal penetration through the barrier layer and the insulating dielectric layer, thereby forming the test specimen; (f) measuring the metal penetration from the metallized blanket layer through the diffusion barrier layer, through the insulating dielectric layer, and into the semiconductor substrate of the test specimen by (1) stripping at least one portion of the insulating dielectric layer, at least one portion of the diffusion barrier layer, and at least one portion of the blanket layer, thereby exposing at least one portion of the semiconductor substrate surface; and (2) examining the exposed at least one portion of the semiconductor substrate surface for the metal penetration, thereby obtaining metal penetration measurement data corresponding to the at least one barrier layer formation parameter; (g) analyzing whether the metal penetration measurement data is within a given tolerance, as quantified, for example, by a diffusion mass flux rate, indicating an acceptable diffusion barrier performance (i.e., de minimis), and, if within the given tolerance, by proceeding to step (h), else adjusting the at least one barrier layer formation parameter and returning to step (a); and (h) fabricating at least one production device using the at least one barrier layer formation parameter, and a test specimen device thereby formed.

Advantages of the present invention include, but are limited to, fabricating a structure which better allows a quantitative determination of Cu penetration (from Cu diffusion) of through barriers and dielectrics (insulators) than does the related art. Unlike the related art "line-to-line leakage" method for characterizing the Cu diffusion, the present invention does not introduce rogue interfaces that create undesirable rapid Cu diffusion pathways around the barrier layer and the dielectric layer, but rather, the present invention measures the Cu diffusion propagating through the diffusion barrier layer and the insulating dielectric layer into the substrate, thereby preventing short-circuiting of the Cu diffusion, and thereby imparting accurate data. In contrast to the related art line-to-line leakage method which merely measures current along the rogue interfaces, the present invention allows for the calculation of mass flux diffusion rate. As such, the present invention provides better characterization of the diffusion properties of the presently claimed barrier layer, comprising advanced barrier materials, when used in conjunction with an insulating dielectric layer (e.g., $SiO_2$ as the dielectric material).

BRIEF DESCRIPTION OF THE DRAWING(S)

For a better understanding of the present invention, reference is made to the below-referenced accompanying drawing(s). Reference numbers refer to the same or equivalent parts of the present invention throughout the drawing(s).

FIG. 1 is a cross-sectional view of a test specimen device comprising: a semiconductor strate, an insulating dielectric layer formed on the substrate, a diffusion barrier layer formed on the insulating dielectric layer, and a metallized blanket layer formed on the diffusion barrier layer, wherein at least one portion of the insulating dielectric layer, at least one portion of the barrier layer, and at least one portion of the blanket layer are removable for testing, in accordance with the present invention.

Figure 2:
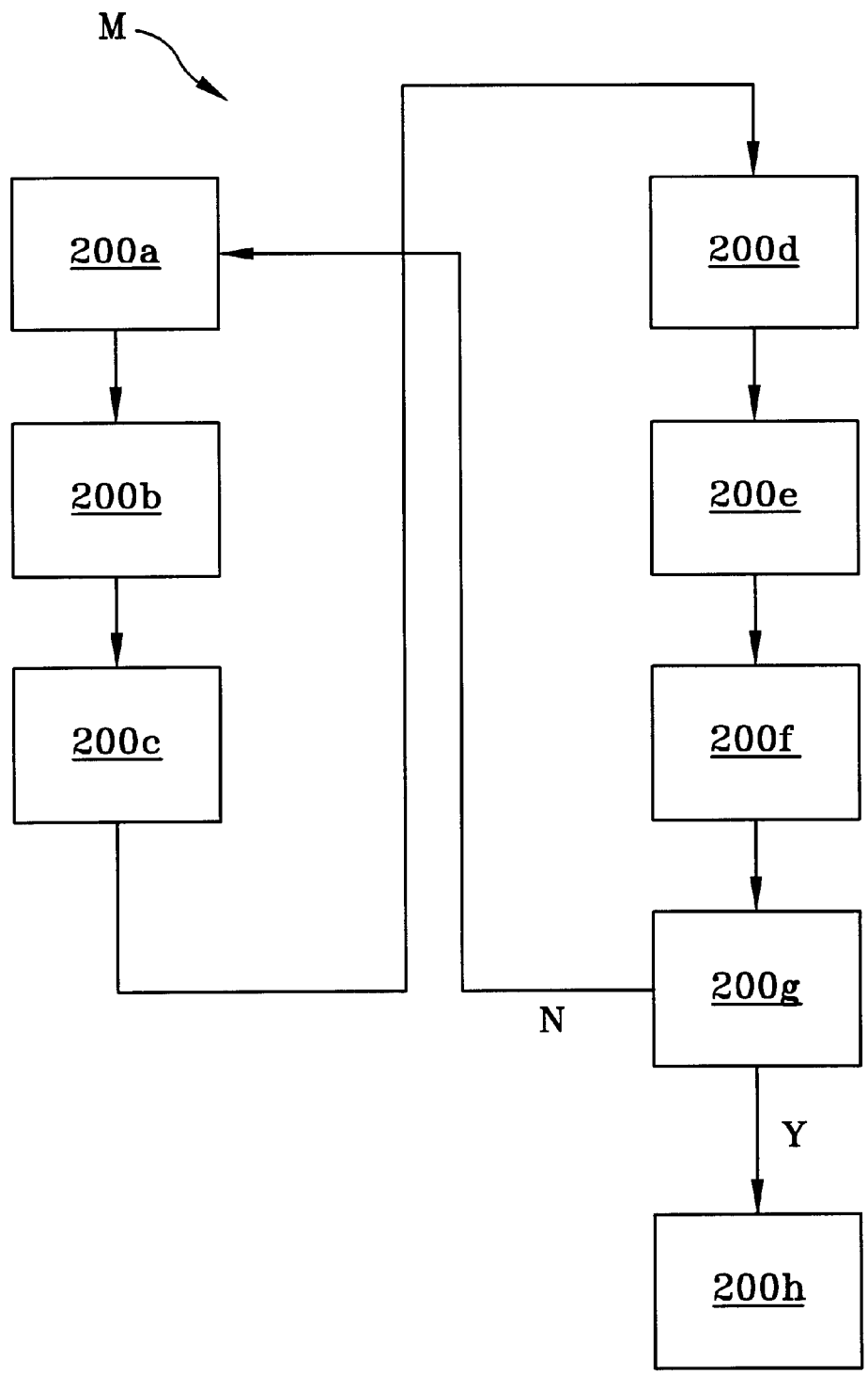

FIG. 2 is a of a method of determining the effectiveness of a diffusion barrier layer by using a test specimen device and measuring the metal penetration from a metallized blanket layer through the diffusion barrier layer, through a thin insulating dielectric layer, and into a semiconductor substrate of a test specimen, thereby obtaining measurement data for fabricating subsequent production devices, in accordance with the present invention.

MODES FOR CARRYING OUT THE INVENTION

FIG. 1 illustrates, by example only, and in cross-section, a test specimen device comprising: a semiconductor substrate 10, an insulating dielectric layer 20 formed on the substrate 10, a diffusion barrier layer 30 formed on the insulating dielectric layer 20, and a metallized blanket layer 40 formed on the diffusion barrier layer 30, where at least one portion 21 of the insulating dielectric layer 20, at least one portion 31 of the barrier layer 30, and at least one portion of the blanket layer 40 are removable for facilitating examination (i.e., detection and monitoring) by a measuring technique 50, in accordance with the present invention.

FIG. 2 flowcharts, by example only, a method M of determining the effectiveness of a diffusion barrier layer 30 by measuring the metal penetration (instigated by accelerated test conditions) from a metallized blanket layer 40 through the diffusion barrier layer 30, through a thin insulating dielectric layer 20, and into a semiconductor substrate 10 of a test specimen, thereby obtaining measurement data for fabricating subsequent production semiconductor devices, in accordance with the present invention. By example only, the present method M comprises the steps of:

(a) providing a semiconductor substrate 10 for forming a test specimen, wherein the substrate 10 preferably comprises silicon (Si), as indicated by block 200a;

(b) forming an insulating dielectric layer 20 on the semiconductor substrate 10,
wherein the insulating dielectric layer 20 preferably comprises at least one dielectric material selected from a group consisting essentially of a thermal silicon dioxide ($SiO_2$) and a deposited silicon dioxide ($SiO_2$), and
wherein the insulating dielectric layer 20 is preferably thin and comprises a thickness in a range of approximately 15 Å to approximately 100 Å, as indicated by block 200b;

(c) forming a diffusion barrier layer 30 on the insulating dielectric layer 20,
wherein step (c) comprises at least one barrier layer 30 deposition parameter,
wherein the barrier layer 30 comprises at least one advanced diffusion barrier material selected from a group consisting essentially of titanium-tungsten (TiW), titanium nitride (TiN), tantalum nitride (TaN), tungsten-carbon-nitride (WCN), refractory metals, such as titanum (Ti), tungsten (W), tantalum (Ta), molybdenum (Mo), their nitrides, and their carbides.
wherein the diffusion barrier layer 30 comprises a continuous barrier layer,
wherein the at least one advanced diffusion barrier material is preferably formed by a technique selected from a group consisting essentially of chemical-vapordeposition (CVD) and atomic layer deposition (ALD), and
wherein the barrier layer 30 is preferably thin and comprises a thickness in a range of approximately 5 Å to approximately 100 Å, as indicated by block 200c;

(d) forming a metallized blanket layer 40 on the diffusion barrier layer 30, wherein the blanket layer 40 preferably comprises copper (Cu), as indicated by block 200d;

(e) treating the blanket layer 40 with at least one technique selected from a group consisting essentially of:
(1) heating the blanket layer 40 in a temperature range of approximately 100° C. to approximately 500° C., preferably approximately 150° C. to approximately 500° C., and
(2) applying a voltage bias to the blanket layer 40 in a range of approximately 0.1 MV/cm electric field to approximately 3 MV/cm electric field, preferably approximately 0.5 MV/cm electric field to approximately 3 MV/cm electric field, for instigating the metal penetration through the barrier layer and the insulating dielectric layer, thereby forming the test specimen, as indicated by block 200e;

(f) measuring the metal penetration from the metallized blanket layer 40 through the diffusion barrier layer 30, through the insulating dielectric layer 20, and into the semiconductor substrate 10 of the test specimen by:
(1) stripping at least one portion of the insulating dielectric layer 20, at least one portion of the diffusion barrier layer 30, and at least one portion of the blanket layer 40, thereby exposing at least one portion of the semiconductor substrate 10 surface; and
(2) examining the exposed at least one portion of the semiconductor substrate 10 surface for the metal penetration, thereby obtaining metal penetration measurement data corresponding to the at least one barrier layer deposition parameter, wherein the examining step is preferably performed by at least one technique 50 selected from a group consisting essentially of a visual inspection, an e-beam imaging technique, a quantitative surface analytical technique, a mass spectroscopy, an x-ray emission technique, an electron spectroscopic surface profiling, and a neutron activation analysis, as indicated by block 200f;

(g) analyzing whether the metal penetration measurement data is within a given tolerance, as quantified, for example, by a diffusion mass flux rate, indicating an acceptable diffusion barrier performance (i.e., de minimis), and, if within the given tolerance, by proceeding to step (h), else adjusting the at least one barrier layer deposition parameter and returning to step (a), as indicated by block 200g; and (h) fabricating at least one production device using the at least one barrier layer deposition parameter, as indicated by block 200h.

INDUSTRIAL APPLICABILITY

The present invention relates to the semiconductor device fabrication industry. In particular, the present invention relates to reducing electromigration in, and reducing copper diffusion copper from, interconnect lines by providing a better barrier layer. More particularly, the present invention applies to the processing of copper interconnect material, such a copper blanket layer, in conjunction with a diffusion barrier layer and the resultant device utilizing the same. Even more particularly, the present invention applies to reducing copper diffusion from copper interconnect lines or blanket layers into the semiconductor substrate by increasing the effectiveness of such barrier layer using an iterative testing process for reducing copper diffusion in subsequent production devices.

SCOPE OF THE INVENTION

Information as herein shown and described in detail is fully capable of attaining the above-described object of the invention, the presently preferred embodiment of the invention, and is, thus, representative of the subject matter which is broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, but rather "one or more." All structural and functional equivalents to the elements of the above-described preferred embodiment and additional embodiments that are known to those of ordinary skill in the art are hereby expressly incorporated by reference and are intended to be encompassed by the present claims.

Moreover, no requirement exists for a device or method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, it should be readily apparent to those of ordinary skill in the art that various changes and modifications in form, semiconductor material, and fabrication material detail may be made without departing from the spirit and scope of the inventions as set forth in the appended claims. No claim herein is to be construed under the provisions of 35 U.S.C. §112, sixth paragraph, unless the element is expressly recited using the phrase "means for."

What is claimed:

1. A method of determining the effectiveness of a diffusion barrier layer using a test specimen for fabricating at least one production semiconductor device, comprising the steps of:

(a) providing a semiconductor substrate for forming a test specimen;

(b) forming an insulating dielectric layer on the semiconductor substrate;

(c) forming a diffusion barrier layer on the insulating dielectric layer, said step (c) comprising at least one barrier layer deposition parameter;

(d) forming a metallized blanket layer on the diffusion barrier layer;

(e) treating the blanket layer with at least one technique selected from a group consisting essentially of:
      (1) heating the blanket layer; and
      (2) applying a voltage bias to the blanket layer, for instigating the metal penetration through the barrier layer and the insulating dielectric layer, thereby forming the test specimen;

(f) measuring the metal penetration from the metallized blanket layer through the diffusion barrier layer, through the insulating dielectric layer, and into the semiconductor substrate of the test specimen by:
      (1) stripping at least one portion of the insulating dielectric layer, at least one portion of the diffusion barrier layer, and at least one portion of the blanket layer, thereby exposing at least one portion of the semiconductor substrate surface; and
      (2) examining the exposed at least one portion of the semiconductor substrate surface for the metal penetration, thereby obtaining metal penetration measurement data corresponding to the at least one barrier layer deposition parameter;

(g) analyzing whether the metal penetration measurement data is within a given tolerance (i.e., de minimis), and, if within the given tolerance, by proceeding to step (h), else adjusting the at least one barrier layer deposition parameter and returning to said step (a); and (h) fabricating at least one production semiconductor device using the at least one barrier layer deposition parameter.

2. A method, as recited in claim 1,
   wherein the step (a) comprises providing the substrate comprising silicon (Si), and
   wherein the step (d) comprises forming the blanket layer comprising copper (Cu).

3. A method, as recited in claim 1, wherein the step (b) comprises forming the insulating dielectric layer comprising at least one dielectric material selected from a group consisting essentially of a thermal silicon dioxide ($SiO_2$) and a deposited silicon dioxide ($SiO_2$).

4. A method, as recited in claim 1, wherein the step (b) comprises forming the insulating dielectric layer being thin and comprising a thickness in a range of approximately 15 Å to approximately 100 Å.

5. A method, as recited in claim 1, wherein the step (c) comprises forming the barrier layer comprising at least one advanced diffusion barrier material selected from a group consisting essentially of titanium-tungsten (TiW), titanium nitride (TiN), tantalum nitride (TaN), tungsten-carbon-nitride (WCN), refractory metals, such as titanum (Ti), tungsten (W), tantalum (Ta), molybdenum (Mo), their nitrides, and their carbides.

6. A method, as recited in claim 1,
  wherein the step (c) comprises forming the barrier layer comprising a continuous barrier layer, and
  wherein the step (c) comprises forming the barrier layer by a technique selected from a group consisting essentially of chemical-vapor-deposition (CVD) and atomic layer deposition (ALD).

7. A method, as recited in claim 1, wherein the step (c) comprises forming the barrier layer being thin and comprising a thickness in a range of approximately 5 Å to approximately 100 Å.

8. A method, as recited in claim 1,
  wherein the step (e)(1) comprises heating the blanket layer in a temperature range of approximately 100° C. to approximately 500° C., and
  wherein the step (e)(2) comprises applying a voltage bias to the blanket layer in a range of approximately 0.1 MV/cm electric field to approximately 3 MV/cm electric field.

9. A method, as recited in claim 1, wherein the step (f)(2) comprises the examining step being performed by at least one technique selected from a group consisting essentially of a visual inspection, an e-beam imaging technique, a quantitative surface analytical technique, a mass spectroscopy, an x-ray emission technique, an electron spectroscopic surface profiling, and a neutron activation analysis.

10. A method of determining the effectiveness of a diffusion barrier layer using a test specimen for fabricating at least one production semiconductor device, comprising the steps of:
  (a) providing a semiconductor substrate for forming a test specimen;
  (b) forming an insulating dielectric layer on the semiconductor substrate;
  (c) forming a diffusion barrier layer on the insulating dielectric layer, said step (c) comprising at least one barrier layer deposition parameter;
  (d) forming a metallized blanket layer on the diffusion barrier layer;
  (e) treating the blanket layer with at least one technique selected from a group consisting essentially of:
    (1) heating the blanket layer; and
    (2) applying a voltage bias to the blanket layer, for instigating the metal penetration through the barrier layer and the insulating dielectric layer, thereby forming the test specimen;
  (f) measuring the metal penetration from the metallized blanket layer through the diffusion barrier layer, through the insulating dielectric layer, and into the semiconductor substrate of the test specimen by:
    (1) stripping at least one portion of the insulating dielectric layer, at least one portion of the diffusion barrier layer, and at least one portion of the blanket layer, thereby exposing at least one portion of the semiconductor substrate surface; and
    (2) examining the exposed at least one portion of the semiconductor substrate surface for the metal penetration, thereby obtaining metal penetration measurement data corresponding to the at least one barrier layer deposition parameter;
  (g) analyzing whether the metal penetration measurement data is within a given tolerance (i.e., de minimis), and, if within the given tolerance, by proceeding to step (h), else adjusting the at least one barrier layer deposition parameter and returning to said step (a); and
  (h) fabricating at least one production semiconductor device using the at least one barrier layer deposition parameter,
    wherein the step (c) comprises forming the barrier layer comprising a continuous barrier layer,
    wherein the step (c) comprises forming the barrier layer by a technique selected from a group consisting essentially of chemical-vapor-deposition (CVD) and atomic layer deposition (ALD), and
    wherein the step (f)(2) comprises the examining step being performed by at least one technique selected from a group consisting essentially of a visual inspection, an e-beam imaging technique, a quantitative surface analytical technique, a mass spectroscopy, an x-ray emission technique, an electron spectroscopic surface profiling, and a neutron activation analysis.

11. A semiconductor test specimen device having an effective diffusion barrier layer, comprising:
  a semiconductor substrate;
  an insulating dielectric layer formed on the semiconductor substrate;
  an effective diffusion barrier layer formed on the insulating dielectric layer;
  a metallized blanket layer formed on the effective diffusion barrier layer,
    the blanket layer comprising a treatment with at least one technique selected from a group consisting essentially of heating the blanket layer and applying a voltage bias to the blanket layer for instigating a metal penetration through the effective barrier layer and the insulating dielectric layer, and
  the substrate comprising the metal penetration for facilitating measurement and analysis for fabricating at least one production semiconductor device.

12. A test specimen device, as recited in claim 11,
  wherein the substrate comprises silicon (Si), and
  wherein the blanket layer comprises copper (Cu).

13. A test specimen device, as recited in claim 11, wherein the insulating dielectric layer comprising at least one dielectric material selected from a group consisting essentially of a thermal silicon dioxide ($SiO_2$) and a deposited silicon dioxide ($SiO_2$).

14. A test specimen device, as recited in claim 11, wherein the insulating dielectric layer is thin and comprises a thickness in a range of approximately 15 Å to approximately 100 Å.

15. A test specimen device, as recited in claim 11, wherein the barrier layer comprises at least one advanced diffusion barrier material selected from a group consisting essentially of titanium-tungsten (TiW), titanium nitride (TiN), tantalum nitride (TaN), tungsten-carbon-nitride (WCN), refractory metals, such as titanum (Ti), tungsten (W), tantalum (Ta), molybdenum (Mo), their nitrides, and their carbides.

16. A test specimen device, as recited in claim 11,
  wherein the barrier layer comprises a continuous barrier layer, and
  wherein the barrier layer is formed by a technique selected from a group consisting essentially of chemical-vapor-deposition (CVD) and atomic layer deposition (ALD).

17. A test specimen device, as recited in claim 11, wherein the barrier layer is thin and comprises a thickness in a range of approximately 5 Å to approximately 100 Å.

18. A test specimen device, as recited in claim 11,
   wherein the blanket layer is heated in a temperature range of approximately 100° C. to approximately 500° C., and
   wherein the blanket layer comprises an applied voltage bias in a range of approximately 0.1 MV/cm electric field to approximately 3 MV/cm electric field.

19. A test specimen device, as recited in claim 11, wherein the examination comprises at least one technique selected from a group consisting essentially of a visual inspection, an e-beam imaging technique, a quantitative surface analytical technique, a mass spectroscopy, an x-ray emission technique, an electron spectroscopic surface profiling, and a neutron activation analysis.

20. A test specimen device, as recited in claim 11,
   wherein the barrier layer comprises a continuous barrier layer,
   wherein the barrier layer is formed by a technique selected from a group consisting essentially of chemical-vapor-deposition (CVD) and atomic layer deposition (ALD), and
   wherein the examination comprises at least one technique selected from a group consisting essentially of a visual inspection, an e-beam imaging technique, a quantitative surface analytical technique, a mass spectroscopy, an x-ray emission technique, an electron spectroscopic surface profiling, and a neutron activation analysis.

* * * * *